US00PP15583P3

(12) United States Plant Patent
Layt

(10) Patent No.: US PP15,583 P3
(45) Date of Patent: Feb. 22, 2005

(54) *LOMANDRA LONGIFOLIA* PLANT NAMED 'LM400'

(50) Latin Name: *Lomandra longifolia*
Varietal Denomination: LM400

(75) Inventor: Todd Anthony Layt, New South Wales (AU)

(73) Assignee: Versascapes, L.L.C., Mt. Pleasant, SC (US)

( * ) Notice: Subject to any disclaimer, the term of this patent is extended or adjusted under 35 U.S.C. 154(b) by 0 days.

(21) Appl. No.: 10/626,680

(22) Filed: Jul. 24, 2003

(65) Prior Publication Data

US 2004/0098777 P1 May 20, 2004

Related U.S. Application Data

(60) Provisional application No. 60/400,389, filed on Jul. 31, 2002.

(51) Int. Cl.[7] ..... A01H 5/00
(52) U.S. Cl. ..... Plt./263
(58) Field of Search ..... Plt./263, 384

(56) References Cited

U.S. PATENT DOCUMENTS

2003/0233692 P1 * 12/2003 Layt ..... Plt./263

OTHER PUBLICATIONS

UPOV–ROM GTITM, Plant Variety Database, 2003/06, GTI Jouve Retrieval Software, Citation for *Lomandra* 'LM400'.*

Australian Government Department of Agriculture, Fisheries and Forestry, Database entry for Australian Plant Breeders Right Application No. 2001/090 for 'LM400.' http://www.affa.gov.au/content/pbr_database/plant_detail.cfm?AID=193762.

Australian Government Department of Agriculture, Fisheries and Forestry, Database entry for Australian Plant Breeders Right Application No. 2001/09 2for 'LM300.' http://www.affa.gov.au/content/pbr_database/plant_detail.cfm?AID=193763.

Gazette entry (Part II) for 'LM300' (Australian Plant Breeders Right Application No. 2001/092) *Plant Varieties Journal* 15:3 (2002).

Gazette entry (Part II) for 'LM400' (Australian Plant Breeders Right Application No. 2001/090), *Plant Varieties Journal* 16:2 (2003).

* cited by examiner

*Primary Examiner*—Anne Marie Grunberg
*Assistant Examiner*—June Hwu
(74) *Attorney, Agent, or Firm*—Myers Bigel Sibley & Sajovec, P.A.

(57) ABSTRACT

'LM400' is a distinctive variety of *Lomandra longifolia* which is characterized by the combination of its dwarf, compact growth habit; its fine, narrow leaf blade; and the blue/grey overall color of the leaf blade.

6 Drawing Sheets

Latin name of the genus and species: The Latin name of the genus and species of the novel variety disclosed herein is *Lomandra longifolia.*

Variety denomination: The inventive variety of *Lomandra* disclosed herein has been given the variety denomination 'LM400'.

BACKGROUND OF THE INVENTION

The present invention relates to a new and distinct perennial variety of *Lomandra longifolia,* which has been given the variety denomination of 'LM400'. Its market class is that of an ornamental grass-like plant. 'LM400' is intended for use in landscaping and as a decorative grass-like plant.

The *Lomandra longifolia* variety 'LM400' was first discovered in January, 1999 in an Australian nursery in the state of New South Wales during a routine inspection of large quantities of *Lomandra longifolia* 'Cassica' (unpatented in the United States; Australian Plant Breeders' Rights Application No. 1997/166) production stock. 'LM400' is believed to be a sport (whole plant) of 'Cassica'. 'LM400' was selected due to its much finer leaf and compact size. 'LM400' was first propagated asexually by division in the state of New South Wales, Australia and has since been asexually propagated by division. The distinctive characteristics of the inventive 'LM400' variety are stable from generation to generation; clones of the variety produced by asexual reproduction maintain the distinguishing characteristics of the original plant.

'LM400' has a dwarf and compact growth habit with leaves that are finer and narrower than *Lomandra longifolia* 'Katrina' (unpatented in the United States; Australian Plant Breeders' Rights Application No. 1997/168), 'Cassica', and common *Lomandra longifolia.* 'LM400' has a more blue/grey overall leaf color than *Lomandra longifolia* 'LM300' (U.S. Plant patent application Ser. No. 10/402,494; Australian Plant Breeders' Rights Application No. 2001/092).

An application for plant breeders' rights for variety 'LM400' has been lodged with the Australian Plant Breeders' Rights Office, and was first gazetted in August 2001 under Application No. 2001/090.

SUMMARY OF THE INVENTION

'LM400' is a distinctive variety of *Lomandra longifolia* which is characterized by the combination of its dwarf, compact growth habit; its fine, narrow leaf blade; and the blue/grey overall color of the leaf blade.

BOTANICAL DESCRIPTION OF THE PLANT

The following is a detailed botanical description of a new and distinct variety of a *Lomandra longifolia* ornamental grass-like plant known as 'LM400'. Plant observations were made on plants grown in New South Wales, Australia. Unless indicated otherwise, the descriptions disclosed herein are based upon observations made in April/May 2002 of mature 'LM400' plants grown in nursery pots and field plots.

Those skilled in the art will appreciate that certain characteristics will vary with older or, conversely, younger plants. 'LM400' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1995 edition.

'LM400' is a perennial, dioecious, *Lomandra longifolia* plant which is believed to be a sport of 'Cassica'. After its selection, 'LM400' was asexually propagated by division. 'LM400' is a narrow-bladed, compact plant, which is unusual for *Lomandra longifolia* plants which typically have a medium-to-wide leaf blade and are larger than 'LM400' is most respects.

Growth Habit, Dimensions and Color

Figure 1:
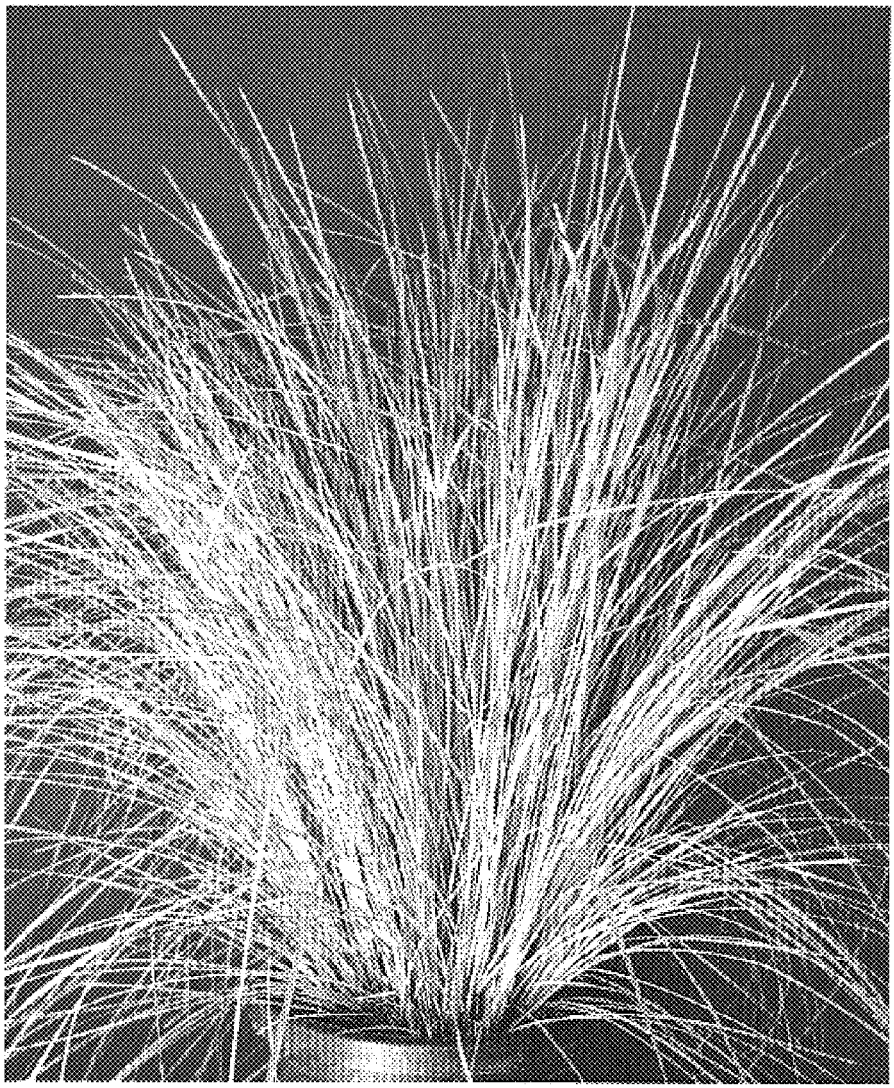
FIG. 1 shows an 'LM400' plant.

'LM400' is a very short, rhizomatous plant forming a compact tussock. Average plant height is 90 cm and average plant spread in 140 cm in a mature plant grown in a 300 mm nursery pot in Sydney, New South Wales, Australia (observed summer–autumn, 2003–2004). The upper and lower side of the leaf is yellow-green RHS 147B (observed summer–autumn 2003–2004) to yellow-green RHS 147A (observed winter 2004) in color. The leaf is generally 3 to 5 mm in width, which is unusual for this species, and reaches an average length of 714 mm. The leaf base is cauline, leaf margin is entire, leaf apex is tridentate and leaf surface texture is strongly glaucous resulting in a blue-grey overall foliage color. The leaf venation pattern is parallel; the color is the same as the rest of the leaf: yellow-green RHS 147B (observed summer–autumn, 2003–2004) to yellow-green RHS 147A (observed winter 2004). The basal shoots are white (RHS 155D) and greyed orange (RHS 164B) in color (observed summer–autumn, 2003–2004). The leaf is generally a uniform width from base to the tip, margins shred at the base, with a tridentate apex typical of *Lomandra longifolia.* Emerging new leaves are flat. A representative 'LM400' plant is shown in FIG. 1.

'LM400' has good color retention in winter compared with other varieties of *Lomandra longifolia,* with the exception of 'LM300' which has better winter color retention then 'LM400'. These features and other characteristics are apparent from the description provided below.

Roots

Similar to other *Lomandra longifolia,* 'LM400' has a massive root structure. The roots are fibrous and spreading, similar to other *Lomandra longifolia.*

Rhizomes

'LM400' has a rhizome which is very short (4.5 cm to 6.5 mm) in a 200 mm pot; rhizome color with the leaf sheath removed is white (RHS 155C); observations made summer–autumn, 2003–2004. Surface texture of the rhizome is smooth.

Bud

Bud shape is oval. Bud color is greyed purple (RHS 183C); observed summer–autumn, 2003–2004.

Inflorescence

The inflorescence is a spike (a panicle of clusters), composed of male flowers. The predominant color of the inflorescence at anthesis is yellow (RHS 6A; observed summer–autumn, 2003–2004), with an average length of 185 mm and an average width of 25 mm. To the touch, the flower spike is medium spiky, which is unusual for this species.

Floret Length

The average length of the floret is 3.3 mm (observed summer–autumn, 2003–2004).

Pedicels

Absent; the florets are sessile.

Bracts

Average bract length is 16 mm; bract color is greyed brown (approximately RHS 199D). Base of bracts often changes to greyed purple (RHS 183A). Observations made in summer–autumn, 2003–2004.

Flowers

Color of outer perianth is greyed purple (RHS 183C) proximally, yellow-green (ranging from RHS 146A to 146B) distally along the central zone, and greyed yellow (RHS 161D) along each perianth segment margin; color of inner perianth is yellow (RHS 6A) fading toward the margin to yellow (RHS 13D). Observations made summer–autumn 2003–2004.

Flower Rachis

The length of the flower rachis is 170–190 mm (observed summer–autumn, 2003–2004).

Reproductive Organs of Male Florets

Six stamens, anther size is 0.5 mm to 0.8 mm in length, anther color is yellow (approximately RHS 8B), observed summer–autumn, 2003–2004.

Seed

Flowers are male; seed is not produced.

Flowering Period

The primary flowering period is in the spring with secondary flowering occurring in summer to autumn in Sydney, New South Wales, Australia.

Lastingness of Bloom

Approximately 9 days in summer flowering in Sydney, New South Wales, Australia.

Fragrance

Fragrance is typical of the species, and of medium strength.

Comparison of 'LM400' with Other Varieties of *Lomandra longifolia*

Figure 2:
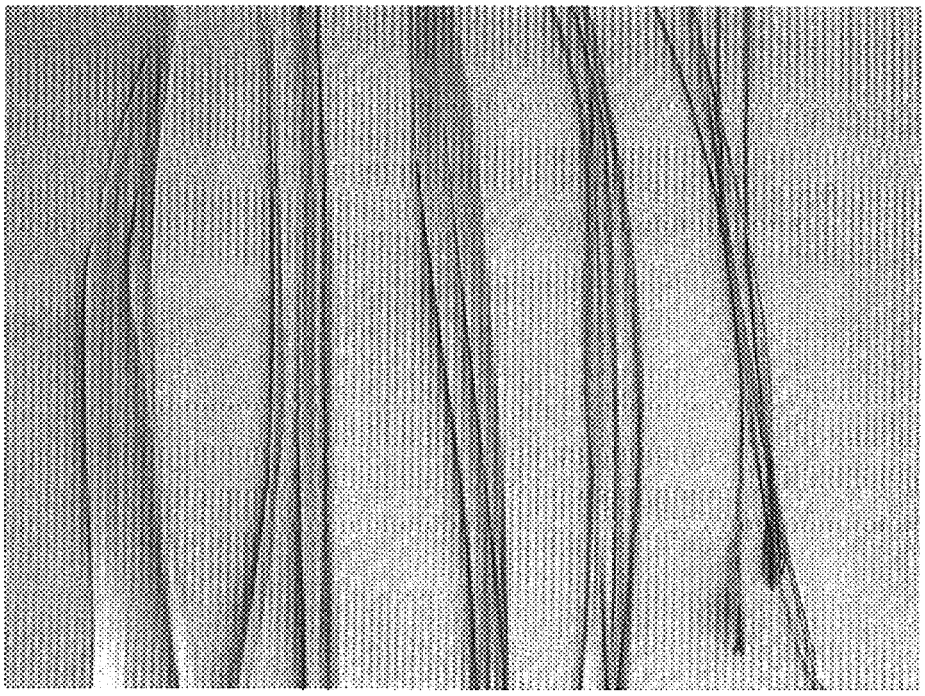
FIG. 2 shows a comparison of the leaf width of 'LM400' with several known varieties of *Lomandra longifolia* plants, from left to right, common *Lomandra longifolia,* 'Katrina', 'Cassica', 'LM400' and 'LM300'.

The leaf blade width of 'LM400' is finer and narrower than that of 'Cassica' and other comparable types of *Lomandra longifolia* (FIG. 2). The blade of 'LM300' is slightly finer and narrower than the blade of 'LM400' (FIG. 3 and FIG. 4).

Figure 5:
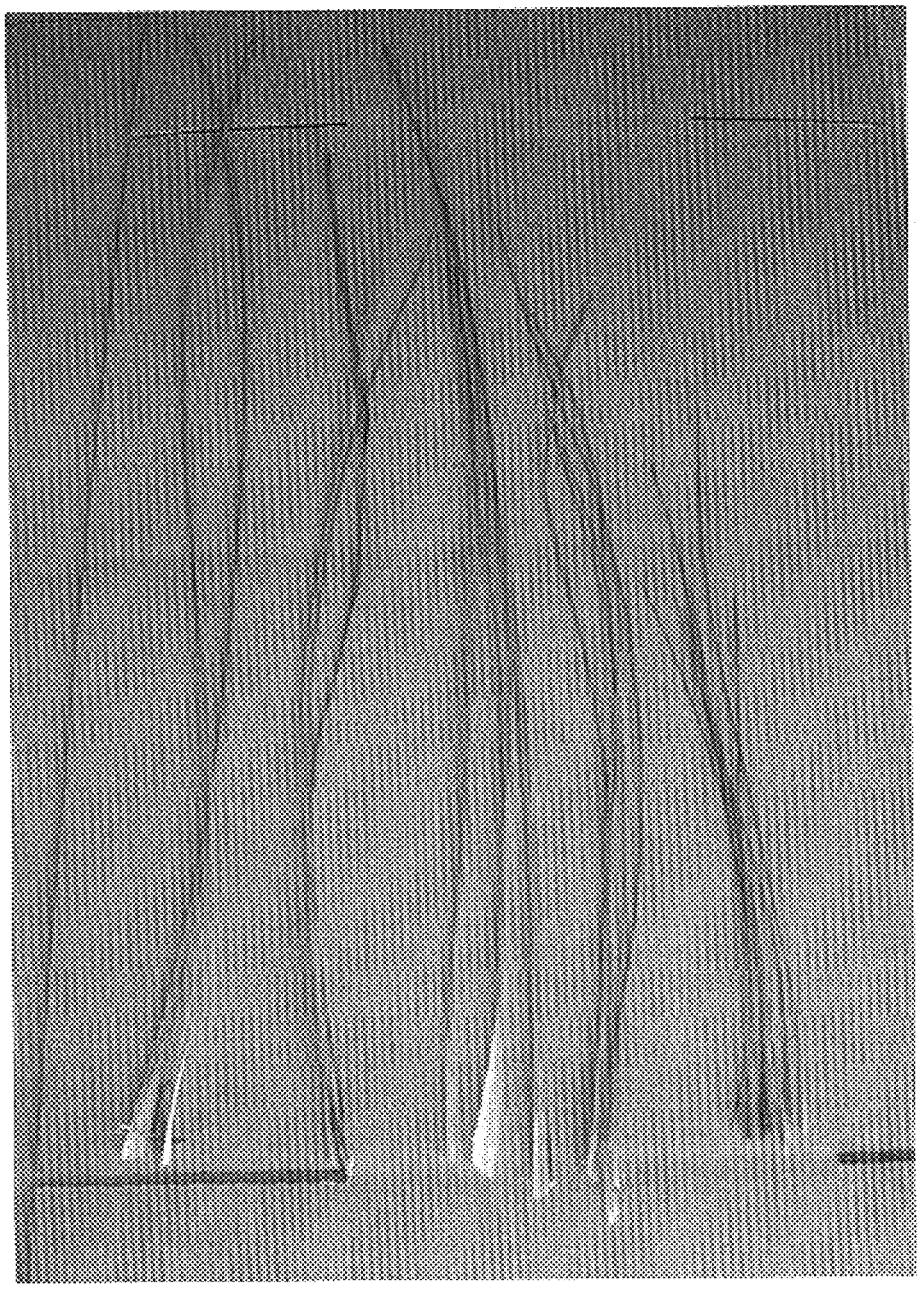
FIG. 5 provides a comparison of the length of the leaf of 'LM400' with several known varieties of *Lomandra longifolia* plants, from left to right, common *Lomandra longifolia,* 'Katrina', 'Cassica', 'LM400' and 'LM300'.

'LM400' also has a more compact habit than 'Katrina', 'Cassica' and other common forms of *Lomandra longifolia* (FIG. 5). 'LM300' is slightly more compact than 'LM400'. The combination of its compact form and narrow leaf makes 'LM400' an attractive ornamental grass-like plant, unlike its parent, which is characterized as a strappy leaf plant.

Figure 3:
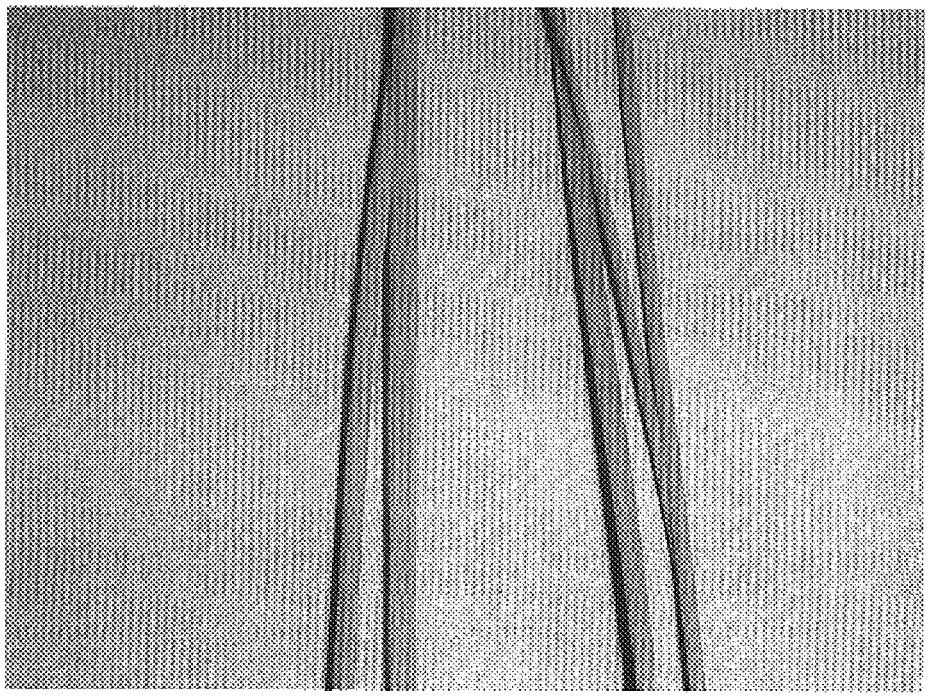
FIG. 3 shows a comparison of the leaf width of 'LM400' (left) and 'LM300' (right).
Figure 4:
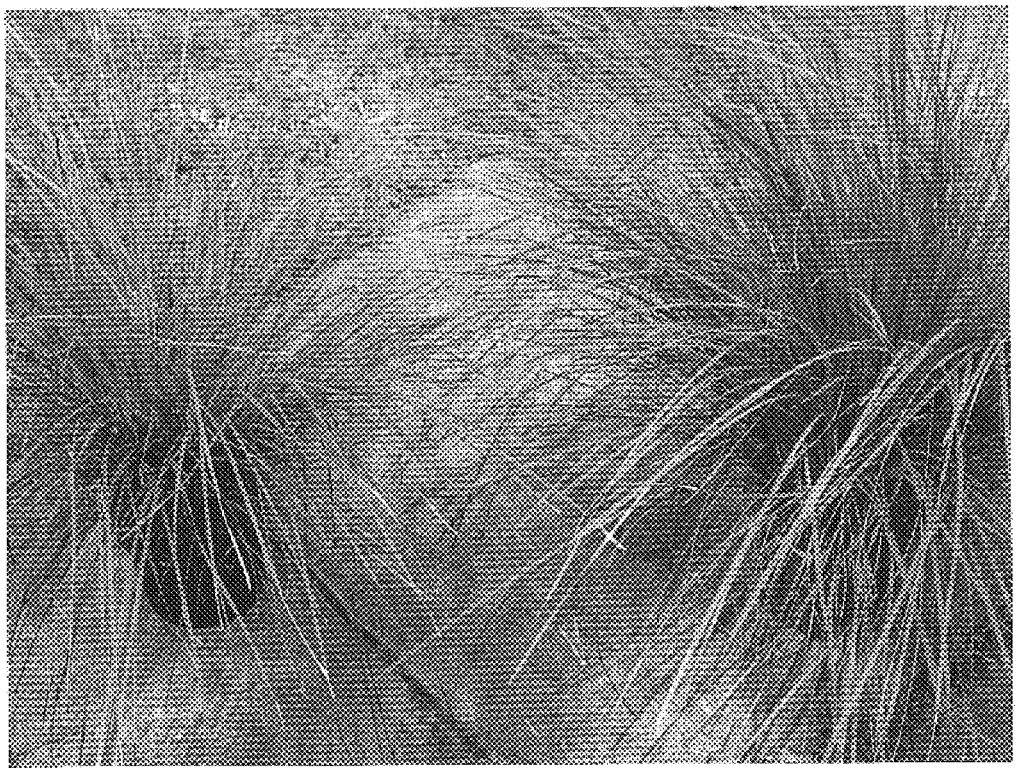
FIG. 4 shows a comparison between 'LM300' (left) and 'LM400' (right) plants.
Figure 6:
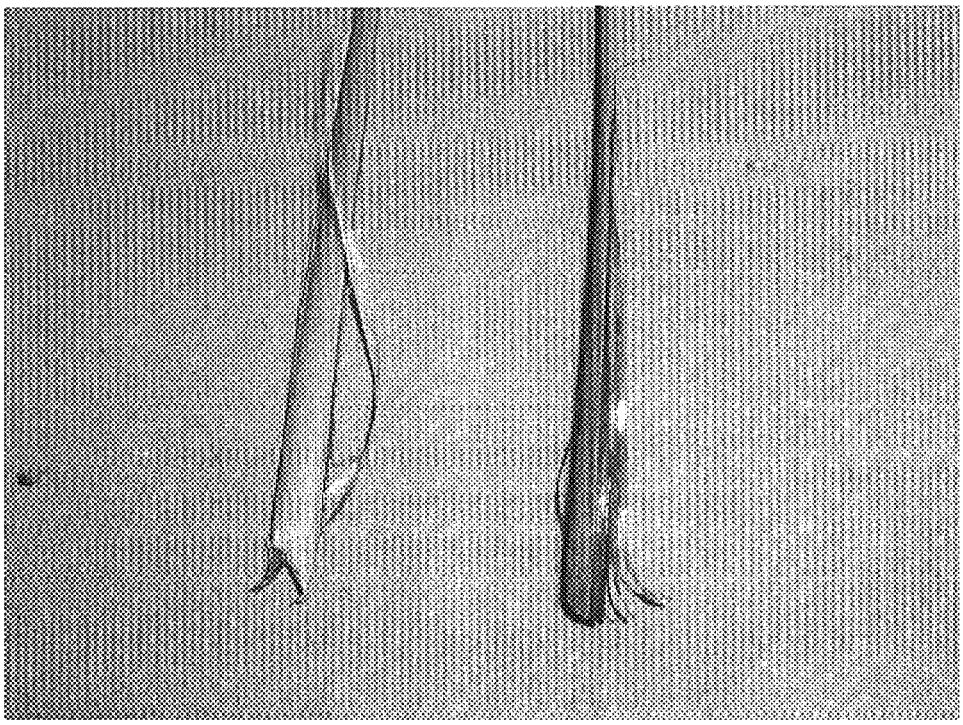
FIG. 6 shows a comparison of the basal shoots of 'LM400' (left) and 'LM300' (right).
Figure 7:
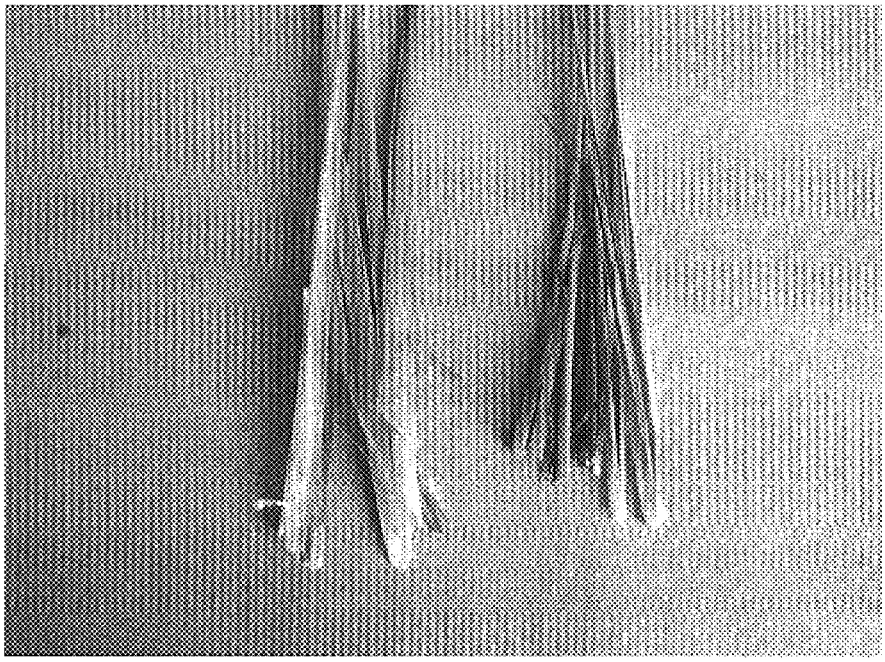
FIG. 7 shows another comparison between the basal shoots of 'LM400' (left) and 'LM300' (right).

The coloration of 'LM400' is distinct from that of 'LM300' (FIG. 3 and FIG. 4). 'LM400' has a blue/grey overall foliage color, whereas 'LM300' has a yellow-green overall foliage color. Furthermore, 'LM300' has greyed orange to greyed purple basal shoots, whilst 'LM400' has white and greyed-orange basal shoots (FIG. 6 and FIG. 7).

Figure 8:
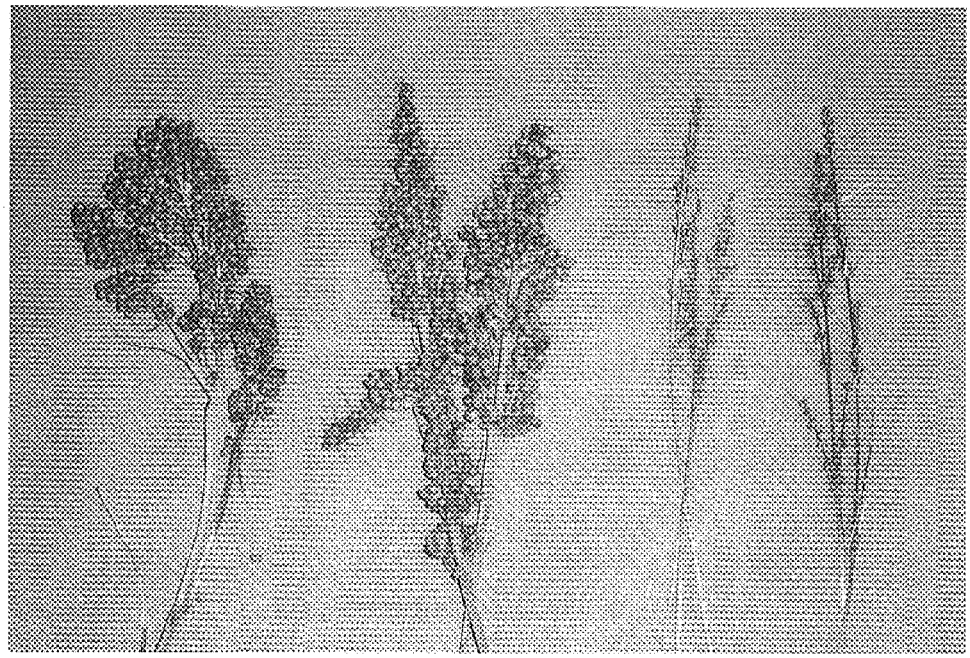
FIG. 8 shows a comparison of the inflorescences of 'LM400' with several known varieties of *Lomandra longifolia,* from left to right, 'Katrina', 'Cassica', 'LM400' and 'LM300'.

'LM400' has a smaller flower spike than 'Katrina' and 'Cassica' (FIG. 8). 'LM400' has a flower spike that is a little shorter than that of 'LM300'. To date, 'LM400' has not produced viable seed, whilst 'Cassica' and 'Katrina' typically produce viable seed in female plants.

The flower spike of 'Katrina' and 'Cassica' are relatively spiky to touch, while the flower spike of 'LM400' is less spiky. 'LM400' is a little spikier than 'LM300' to touch.

The novelty and distinctiveness of 'LM400' as compared with other varieties of *Lomandra longifolia* is further illustrated by vegetative (Table 1) and inflorescence (Table 2) measurements and characteristics.

TABLE 1

| Variety | Blade Width (mm) | Basal Shoot Membrane Color | Blade Length* (mm) | Overall Foliage Color | Strength of Leaf Glaucosity |
|---|---|---|---|---|---|
| 'LM300' | 2.5 to 3.5 | Purple/ Dark Brown | 557.5 | Yellow-Green | Weak-Medium |
| 'LM400' | 3 to 5 | White & Greyed Orange | 714 | Blue/Grey | Strong |
| 'Katrina' | 7 to 10 | Purple | 947.5 | Green | Medium |
| 'Cassica' | 10 to 15 | White/ Green | 1095 | Blue/Grey | Medium-Strong |
| Common Lomandra# | 10 to 16 | Variable | 1085 | Green-Blue/Grey | Medium to Medium-Strong |

*Indicates average.
#Not subject to Australian Plant Breeder's Rights.
Test Plots were planted on July 6, 2001 at Abulk Nursery in Windsor, New South Wales, Australia by Abulk Pty Ltd.

TABLE 2

| Variety | Flower Spike Length* (mm) | Flower Spike Width* (mm) | Spikiness |
|---|---|---|---|
| 'LM300' | 195 | 25 | Very Little Spikiness |
| 'LM400' | 185 | 25 | Medium Spikiness |
| 'Katrina' | 240 | 65 | Medium to Very Spiky |
| 'Cassica' | 230 | 48 | Very Spiky |
| Common Lomandra# | 240 | 51 | Very Spiky |

*Indicates average.
#Not subject to Australian Plant Breeder's Rights.
Test Plots were planted on July 6, 2001 at Abulk Nursery in Windsor, New South Wales, Australia by Abulk Pty Ltd.

Asexual Reproduction

After its initial discovery, 'LM400' was transplanted into a 140 mm pot for further trials and testing. After divisions were made for several subsequent generations, 'LM400' was observed to retain color, size, and fine leaf characteristics that were noted in the original 'LM400' seeding. 'LM400' was then divided into many larger pots for further evaluation.

During these divisions, it was noted that 'LM400' could produce 5 to 8 divisions per 140 mm pots. In comparison, 'Katrina', 'Cassica' and common *Lomandra longifolia* only produced 2 to 5 divisions. More extensive data regarding division rates per 140 mm pot and 300 mm pot of 'LM400' as compared with other *Lomandra longifolia* are presented in Table 3.

TABLE 3

| Variety | Divisions per 140 mm Pot (Range) | Divisions per 300 mm Pot (Range) |
|---|---|---|
| 'LM300' | 7 to 10 | 24 to 32 |
| 'LM400' | 5 to 8 | 22 to 26 |
| 'Katrina' | 4 to 5 | 8 to 13 |
| 'Cassica' | 2 to 3 | 6 to 7 |
| Common Lomandra* | 2 to 3 | 6 to 9 |

*Not subject to Australian Plant Breeder's Rights.
Test Plots were located at Abulk Nursery in Windsor, New South Wales, Australia.
Divided between July 6, 2001 and December 15, 2001.

Divisions of 'LM400' root within 3 to 4 weeks, which is faster than the 5 to 7 weeks typical for 'Cassica'. The survival rate of 'LM400' division is 97% whilst 'Cassica' is approximately 80%. A more detailed comparison of division survival rate is provided in Table 4.

TABLE 4

| Variety | No. of Divisions that Survived Out of 200 |
|---|---|
| 'LM300' | 198 |
| 'LM400' | 194 |
| 'Katrina' | 170 |
| 'Cassica' | 159 |
| Common Lomandra* | 163 |

*Not subject to Australian Plant Breeder's Rights.
Test Plots were located at Abulk Nursery in Windsor, New South Wales, Australia.
Divided between July 6, 2001 and December 15, 2001.
Potting mix used contained 50% sand and 50% peat. Plants were divided into 90 mm × 50 mm × 50 mm tubes.

Environmental Tolerances

'LM400' has shown potential for shade tolerance and further shade tolerance tests are underway. The winter hardiness of 'LM400' is at least to zone 8a in the Southeastern United States, and evaluation of winter hardiness is ongoing. 'LM400' has been observed to hold color to −8 degrees Celsius without any noticeable change in appearance of the plant. With testing at −12 degrees Celsius, minor frost burning was observed at the tips of the leaves, with slight paling in color. 'LM400' has excellent drought tolerance compared with other *Lomandra longifolia* varieties, most likely due to the massive, deep root system. After severe wilting, 'LM400' has been noted to recover with watering. 'LM400' does well in sandy soils, but also tolerates heavy, clay-type soils well.

Disease Resistance

'LM400' has good resistance to root rot compared with most other *Lomandra longifolia,* but is not as resistant as 'LM300'.

That which is claimed is:

1. A new and distinct variety of *Lomandra longifolia* plant named 'LM400', substantially as described and illustrated herein.

* * * * *